United States Patent [19]

Tuzson

[11] 4,442,707

[45] Apr. 17, 1984

[54] METHOD AND CENTRIFUGAL APPARATUS FOR SLURRY EROSION TESTING

[75] Inventor: John J. Tuzson, Evanston, Ill.

[73] Assignee: Allis-Chalmers Corporation, Milwaukee, Wis.

[21] Appl. No.: 451,556

[22] Filed: Dec. 20, 1982

[51] Int. Cl.³ .............................................. G01N 3/56
[52] U.S. Cl. ............................................. 73/86; 73/7
[58] Field of Search ....................................... 73/7, 86

[56] References Cited

U.S. PATENT DOCUMENTS 4,143,539  3/1979  Baillie ........................................ 73/7

FOREIGN PATENT DOCUMENTS 142459  3/1961  U.S.S.R. .................................... 73/7
892273  12/1981  U.S.S.R. .................................... 73/7

*Primary Examiner*—S. Clement Swisher
*Attorney, Agent, or Firm*—Lee H. Kaiser

[57] ABSTRACT

In accordance with the centrifugal erosion testing method of the invention, a material specimen is rotated with a flat surface facing the direction of rotation and a narrow stream of an abrasive particle slurry is concurrently flowed at a preselected rate in a radial direction across the flat surface, the rotating step being at sufficiently high angular velocity to urge the abrasive particles by Coriolis acceleration into a compacted mass against the flat surface and erode material therefrom by scouring type action as the particles flow radially outward. The rotating and flowing steps are continued for a sufficient preselected duration to erode material to a measurable depth, and the depth to which the flat surface is worn by the abrasive particles is measured as an indication of the erosion resistance of the specimen material. The centrifugal slurry erosion testing apparatus includes a rotatable cylindrical vessel into the interior of which the abrasive slurry is fed and a specimen holder extending radially from the vessel having a cavity for receiving the specimen and a radial slurry flow passage communicating with the interior of the vessel. One of the radial passage longitudinal walls is defined by the flat surface of the specimen. Preferably the specimen holder comprises mating semicylindrical halves one of which has a specimen-receiving cavity in its abutting surface and the other has a narrow rectangular-in-cross section groove in its abutting surface which communicates with the interior of the vessel and together with the flat surface of the specimen defines the radial slurry flow passage. The mating semicylindrical halves are enclosed by a sleeve having an annular rim disposed interiorly of the vessel to prevent radially outward movement of the specimen holder.

11 Claims, 4 Drawing Figures

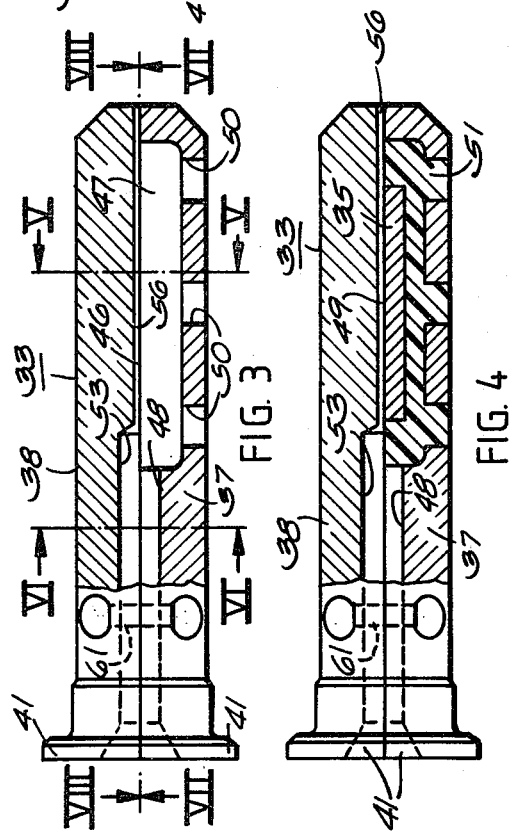

| MATERIAL TESTED | 1070 STEEL | | 1018 MILD STEEL | | ALLOY 92 | |
|---|---|---|---|---|---|---|
| BRINELL HARDNESS | 247 | | 186 | | 550 | |
| ROTOR SPEED (RPM) | 1810 | | 1810 | | 1810 | |
| FLOW RATE (GPM) | 2.0 | | 2.0 | | 2.0 | |
| TIME (SECONDS) | 910 | | 900 | | 1200 | |
| TYPE OF SLURRY | AL-OXIDE | | AL-OXIDE | | AL-OXIDE | |
| SIZE OF SLURRY | #180 MESH (86.4μ) | | #180 MESH (86.4μ) | | #180 MESH (86.4μ) | |
| CONCENTRATION (%) | 7.377 | | 7.50 | | 7.413 | |
| (A) DISTANCE FROM TIP | 0.5" | | 0.5" | | 0.5" | |
| WEAR WIDTH/DEPTH | .0505 | .004 | .045 | .006 | .052 | .0015 |
| (B) DISTANCE FROM TIP | 1.0" | | 1.0" | | 1.0" | |
| WEAR WIDTH/DEPTH | .050 | .00375 | .042 | .005 | .051 | .0015 |
| (C) DISTANCE FROM TIP | 1.5" | | 1.5" | | 1.5" | |
| WEAR WIDTH/DEPTH | .0465 | .0024 | .047 | .0025 | .049 | .0009 |
| $E_{sp}$ (A) $\frac{ENERGY}{VOLUME}\left(\frac{LB.-IN.}{IN.^3}\right)$ | $.94286 \times 10^8$ | | $.70928 \times 10^8$ | | $3.2356 \times 10^8$ | |
| $E_{sp}$ (B) $\frac{ENERGY}{VOLUME}\left(\frac{LB.-IN.}{IN.^3}\right)$ | $.92345 \times 10^8$ | | $0.8290 \times 10^8$ | | $2.999 \times 10^8$ | |
| $E_{sp}$ (C) $\frac{ENERGY}{VOLUME}\left(\frac{LB.-IN.}{IN.^3}\right)$ | $1.3963 \times 10^8$ | | $1.3335 \times 10^8$ | | $4.6823 \times 10^8$ | |

FIG. 11

METHOD AND CENTRIFUGAL APPARATUS FOR SLURRY EROSION TESTING

BACKGROUND OF THE INVENTION

Erosion in pumps and stationary flow passages from slurry particles is of great importance in equipment for wet mineral and coal beneficiation processes. Since the operating conditions and materials vary and are difficult to monitor in the field, only general guidelines on wear can be expected from operating experience.

The scale of the wear process is of the order of the particle size involved, which typically is 0.1 mm (0.004 inches). Larger particles may be present in the slurry, but their number in contact with the passage walls is small. Local wear on such a scale can be tested in the laboratory and then extrapolated to full-size equipment if the laboratory conditions are closely controlled to provide an absolute value of wear rate and if local flow conditions can be calculated in full-size equipment.

Wear test fixtures of the jet inpingement type and of the paddle wheel type are known and are useful development tools. However, local flow conditions are not precisely controlled and cannot be easily calculated or analyzed in such wear test devices. Further, such test fixtures are unsuitable for testing materials of very high wear resistance because of the excessive testing time required, deterioration of the test equipment and attrition of slurry particles. More important, such test devices do not model the particular wear mechanism encountered in slurry systems.

OBJECTS OF THE INVENTION

It is an object of the invention to provide an improved centrifugal slurry wear test method and apparatus which more closely models the wear mechanism that is encountered in slurry systems than prior art devices. It is a further object to provide such improved centrifugal slurry wear test method and apparatus which permits local flow conditions to be closely controlled and flow and erosion rates to be readily calculated.

It is a further object of the invention to provide an improved centrifugal slurry wear test method and apparatus which flows a compacted layer of abrasive particles along the surface of a material specimen to be tested and forces such particles against the surface by Coriolis acceleration under closely controlled conditions to remove material from the speciman to a measurable depth in a scouring type of wear that simulates the wear mechanism encountered in slurry systems and permits the wear rate to be readily calculated.

SUMMARY OF THE INVENTION

In accordance with the method of invention, a test specimen is rotated with a flat surface facing the direction of roation, and a narrow stream of an abrasive slurry is flowed in a radial direction over the flat surface, the angular velocity being sufficiently high so the abrasive particles are subjected to Coriolis acceleration and flow in a compacted layer along such surface and wear material therefrom to a measurable depth in a scouring type of action that simulates the wear mechanism encountered in slurry systems. Preferably the specimen is rotated at a preselected rpm, and a preselected volume of slurry is flowed against the specimen.

The improved centrifugal wear test apparatus of the invention includes a rotatable vessel; means for feeding a slurry of abrasive particles into the vessel; a specimen holder extending radially from the vessel comprising first and second abutting members the first of which has a narrow radially extending groove in the abutting surface communicating with the interior of the vessel and the second of which has a cavity in its abutting surface for receiving a test specimen with a flat surface of the specimen facing the direction of rotation and together with the groove in the first member defining a radially extending channel to which the flat surface of the test specimen is exposed; and means for rotating the vessel carrying the specimen holder at preselected high angular velocity so the abrasive particles in the slurry flow through the radial channel and are urged by Coriolis acceleration to form a compacted layer against the flat surface of the specimen which removes material therefrom to a measurable depth by scouring action, which depth is indicative of the erosion resistance of the material of the specimen. Preferably the radial channel is rectangular in cross section and the specimen is rigidly cemented in the cavity.

DESCRIPTION OF THE DRAWINGS

The above and other objects and advantages of the invention will be more readily apparent from consideration of the following detailed description together with the accompanying drawing wherein:

FIG. 3 is a top view of the specimen holder and is shown partly in section to illustrate the structure of the two mating halves without the test specimen therein;

FIG. 4 is a view similar to FIG. 3 with the test specimen assembled in the specimen holder;

FIGS. 5 and 6 are views taken along lines V—V and VI—VI of FIG. 3 respectively;

FIGS. 7 and 8 are views taken along lines VII—VII and VIII—VIII of FIG. 3 respectively;

FIG. 11 is a table showing the results of typical slurry erosion tests conducted on three different materials in accordance with the method and apparatus of the invention.

DETAILED DESCRIPTION OF PREFERRED EMBODIMENTS

Figure 1:
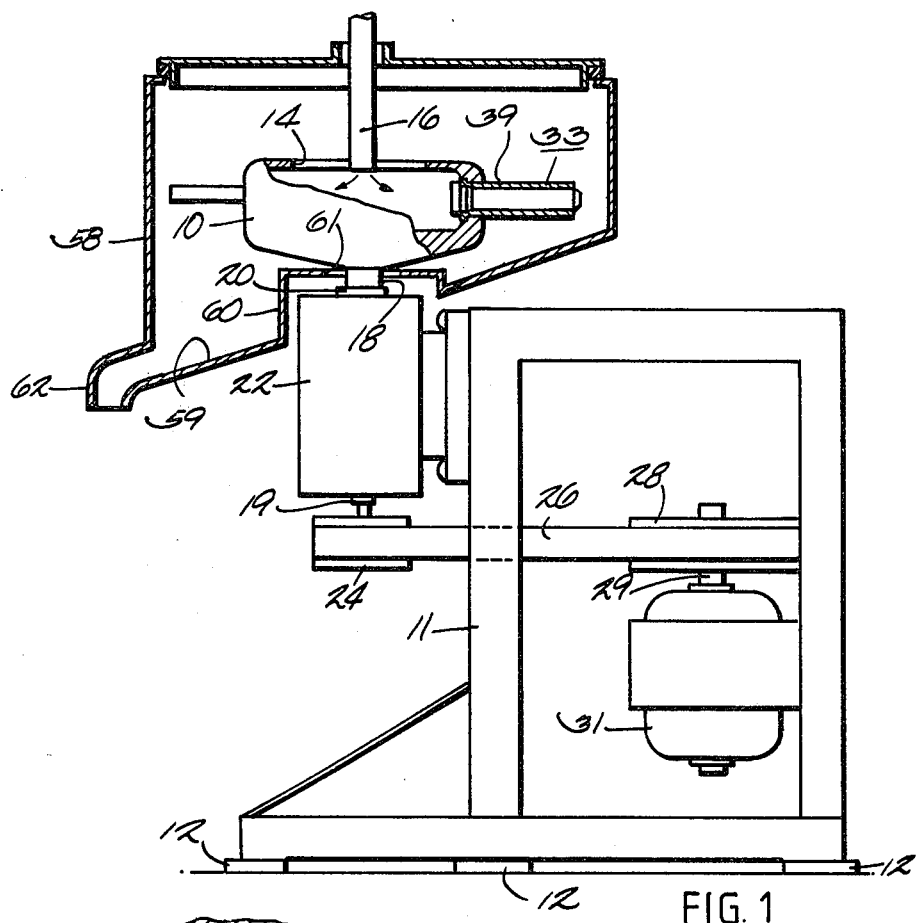
FIG. 1 is a side view of a preferred embodiment of a slurry erosion test fixture embodying the invention, parts being broken away to illustrate the internal construction.
Figure 2:
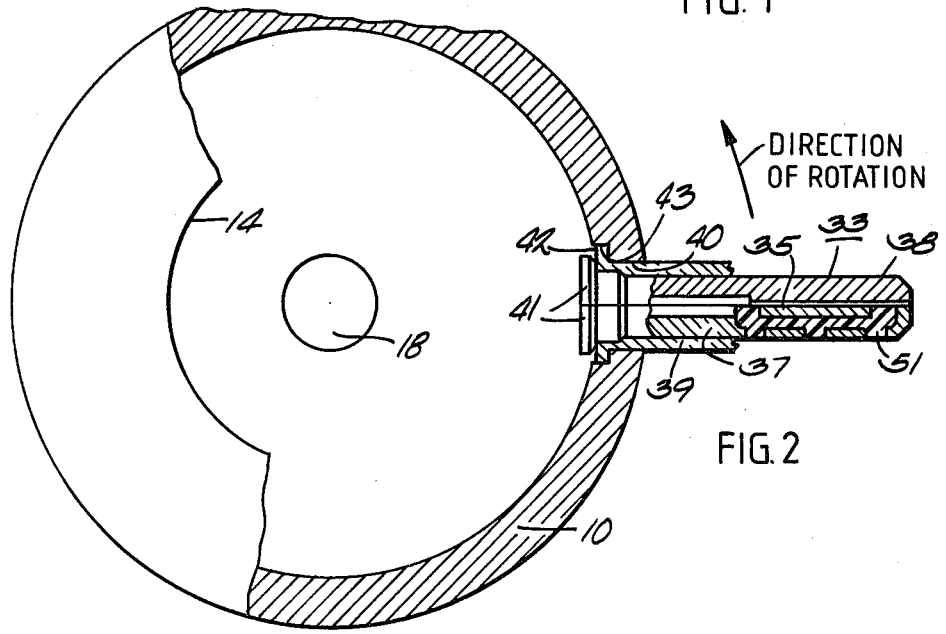
FIG. 2 is a partial top view of the rotating bowl shown in FIG. 1 with parts broken away to illustrate the mounting of the specimen holder.
Figure 9:
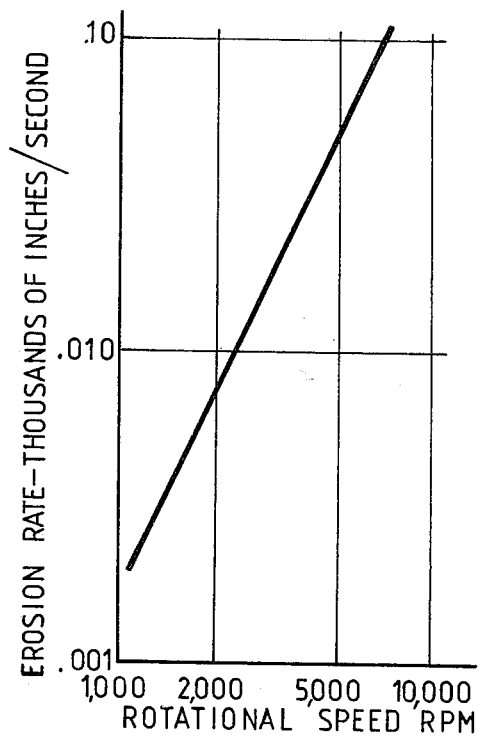
FIG. 9 is a curve plotting erosion rate of a mild steel test specimen versus rotational speed at 15% slurry concentration and 0.5 gallons per minute flow rate.

A centrifugal slurry erosion test fixture embodying the invention shown in FIG. 1 has a cylindrical hollow vessel, or bowl 10 disposed with its axis vertical and rotatably supported from an angle iron framework 11 which rests upon a plurality of feet 12. Bowl 10 may have an opening 14 in its upper surface through which a vertical pipe 16 depends to introduce, or feed downward into the center of bowl 10 a slurry of abrasive particles from an overhead stirred tank (not shown). Bowl 10 at its lower end may taper to a neck portion 18 which is secured to the upper end of a vertically disposed shaft 19 supported for rotation in suitable bearings 20 in a bearing support structure 22 mounted on framework 11. A pulley 24 secured to the lower end of shaft 19 engages a belt 26 which is driven by a drive pulley 28 affixed to the shaft 29 of an electric drive motor 31 mounted on framework 11.

A specimen holder 33 carrying a specimen 35 of material to be wear tested is affixed to and projects radially from the sidewall of bowl 10. Specimen holder 33 preferably comprises two mating halves in the form of first and second abutting semicylindrical members 37 and 38 encased in a tubular sleeve 39. Sleeve 39 preferably projects through an opening 40 in the sidewall of bowl 10 and has an outwardly extending rim 42 at its radially inner end which nests within an annular groove 43 in the interior surface of the sidewall of bowl 10 to prevent radially outward movement of sleeve 39 carrying specimen holder 33. Assembled first and second semicylindrical members 37 and 38 preferably have outwardly projecting semicircular portions 41 at their inner ends which abut against rim 42 of sleeve 39 to prevent radially outward movement of specimen holder 33 when bowl 10 is rotated.

First semicylindrical member 37 of specimen holder 33 is preferably of a highly wear resistant material such as hardened steel, rubber or a ceramic material. Member 37 has a flat surface 46 with an elongated cavity, or depression 47 therein adjacent its radially outer end for receiving specimen 35 of the material to be wear tested and also has a semicylindrical groove 48 radially inward from cavity 47 which communicates with the interior of bowl 10 and partially defines a longitudinal passage for radial flow of the slurry. Test specimen 35 (see FIG. 4) has a flat surface 49 which is transverse to and faces the direction of rotation of bowl 10 when the abutting halves 37 and 38 of specimen holder 33 are assembled within sleeve 39. The size of flat surface 49 of test specimen 35 may, for example, be approximately 1.5 inches by 0.44 inches. First member 37 has a plurality of apertures 50 which register with cavity 47 to permit a suitable adhesive material, or cement such as epoxy resin 51 to be poured from the exterior of member 37 into depression 47 and around test specimen 35 while the specimen is inserted into depression 47.

Second semicylindrical member 38 is also preferably of highly wear-resistant material. During wear testing second member 38 has its flat surface 52 transverse and opposite to the direction of rotation of bowl 10. A groove extending longitudinally of flat surface 52 has a semicylindrical portion 53 adjacent its radially inner end opposite semicylindrical groove 48 in member 37 to define a cylindrical passage for radial flow of slurry when halves 37 and 38 are mated. Opposite cavity 47 the groove is reduced to a shallow, narrow rectangular-in-cross section portion 55 (for example, 0.04 inches wide by 0.04 inches deep) which together with flat surface 49 of test specimen 35 define a rectangular channel 56 for radially outward flow of the slurry from within bowl 10 while it is rotated by motor 31 and belt 26. Mating alignment holes 57 are provided in first and second members 37 and 38. Dowel pins 61 are affixed within the alignment holes 57 in one half 37 or 38 and fit within the alignment holes 57 in the other half to hold the two halves 37 and 38 of specimen holder 33 in alignment.

Bowl 10 is rotated at speed up to 7,200 rpm in order to simulate the wear mechanism of test specimen 35 that is encountered in slurry systems but to accelerate the wear rate. The slurry may be a liquid mixture of abrasive particles such as aluminum oxide particles of 200 mesh = 80 micron size at concentrations of up to 20% by weight. The slurry particles are urged outward by centrifugal force through radial rectangular-in-cross section channel 56 and are subjected to Coriolis acceleration therein and form an abrasive layer against the leading face of channel 56 (which is partially defined by flat surface 49 of test specimen 35).

It is believed that wear of test specimen 35 by the abrasive particles is of the scouring type in which a compacted layer of the particles is pressed against flat surface 49 of test specimen 35 by the Coriolis acceleration forces and dragged along by the mainstream so material is removed from flat surface 49 by a plowing and shearing process which resembles the action of sandpaper (except that the slurry particles are not fully restrained and can tumble to some extent). The flow velocity of the slurry and the Coriolis acceleration can be accurately controlled and readily calculated.

A shroud 58 surrounding bowl 10 has a downwardly inclined bottom wall 59 with an upwardly extending annular neck portion 60 having a circular opening 61 which freely receives neck portion 18 of bowl 10. Slurry flowing through channel 56 impinges on the sidewall of shroud 58 when it is emitted from specimen holder 33 and flows downwardly along bottom wall 59 which terminates in a slurry return spout 62 from which the slurry is recirculated to the overhead tank.

Bowl 10 is rotated at a predetermined rpm during the wear test and the duration of the test is preselected. Typical test duration against a mild steel test specimen 35 is 4 to 9 minutes and results in an erosion depth of 0.005 to 0.02 inches (0.129 to 0.5 mm). Wear of test specimen 35 may evidence corner vortices at the entrance to channel 56 but these die out, and the wear of specimen 35 radially outward from the entrance is uniform across the width of channel 56 and usually shows a ripple pattern which is typical of scouring action. The width and average depth of the erosion groove in test specimen 35 is measured at different radial distances from the center of rotation, for example, at 4.5", 5.0" and 5.5" from the center of rotation (which may, for example, be 0.5", 1.0" and 1.5" from the radial inner tip of the test specimen 35).

The slurry erosion wear resistance of a test specimen material to a specific slurry material is characterized by the Specific Energy $E_{sp}$ which is the energy that must be expanded to remove a unit volume of material and has the dimensions of in. lb./in$^3$. It is an absolute measure of wear resistance independent of the test fixture used. In the method and test fixture of the invention, the slurry is flowing in a rectangular radial channel 56 while the specimen 35 being rotated, as schematically represented by angular velocity symbol $\omega$ in the erosion model of FIG. 10. The abrasive particles are subjected to Coriolis acceleration and settle against the leading face of the channel wall, which is defined by the flat surface 49 of test specimen 35. It is assumed that an equilibrium condition has been reached where the abrasive particles form a layer of thickness Y and with maximum packing density that flows radially outward at velocity u, but the forces are transmitted from one particle to the next as if it were a solid.

Figure 10:
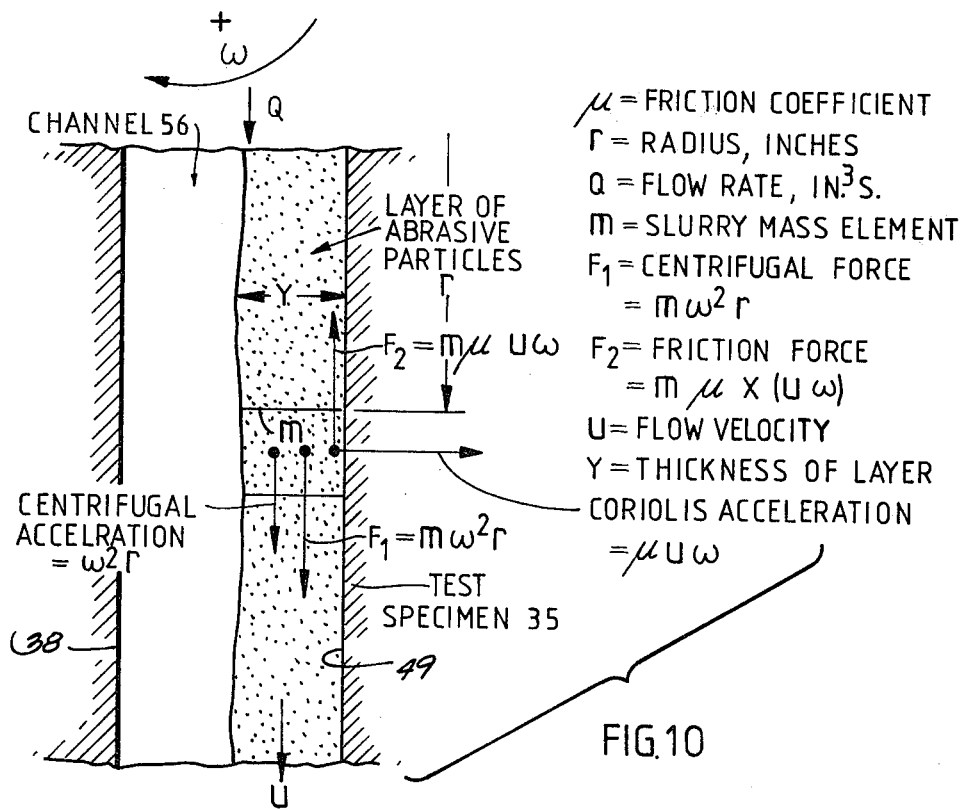
FIG. 10 is a schematic representation of an erosion model of the test specimen and rectangular radial slurry flow channel and illustrates the direction of the forces.

The mass flow rate of abrasive particles, corrected for submergence in water, passing over a unit area of surface 49 of test specimen 35 must be multiplied by the Coriolis acceleration (uω) and the friction coefficient (μ) to calculate the energy dissipated per unit time over the unit area. For the particular flow geometry of the test fixture of the invention (which flow geometry is schematically represented in FIG. 10) the centrifugal force acting on a unit particle mass m may be expressed as $m\omega^2 r$ and is equal to the radial friction force $F_2 = m\mu u\omega$. The centrifugal acceleration of the abrasive particles in a radial direction ($\omega^2 r$) is equal to the Coriolis acceleration (uω) multiplied by the friction coefficient:

$$\omega^2 r = \mu u \omega$$

where

ω = is the angular velocity
r = distance from center of rotation
μ = friction coefficient
u = flow velocity Consequently the friction coefficient and the Coriolis acceleration need not be calculated separately but can be replaced by the centrifugal acceleration ($\omega^2 r$). The mass flow rate of solid material is represented by $(\rho_s - \rho_l)(C_o/C_m)(Q/h)$ where:

$\rho_s$ = density of solid
$\rho_l$ = density of slurry liquid
$C_o/C_m$ = ratio of inlet volume fraction to volume percentage at maximum packing
Q = flow rate, in.$^3$/s.
h = width of slurry passage in.

and is multiplied by the centrifugal acceleration ($\omega^2 r$) to yield the energy dissipated per unit area of wear surface = $(\rho_s - \rho_l)(C_o/C_m)(Q/h)\omega^2 r$. The Specific Energy $E_{sp}$ which must be expended to erode a unit volume of material from surface 49 of the test specimen 35 is then equal to the energy dissipated per unit surface area divided by the volume of material removed per unit time (t/s) over the wear area (where s equals wear depth in inches and t is wear time in seconds), or $$E_{sp} = \text{(Energy)/(Volume removed)} =$$
$$(\rho_s - \rho_l)(C_o/C_m)(Q/h)\omega^2 r\,(t/s) \text{ in.-lb./in.}^3$$

In the disclosed slurry erosion test fixture the energy dissipation and the wear rate of the specimen are very uniform and can be easily, reliably, and accurately measured. Consequently the disclosed slurry erosion test device provide an accurate value of the Specific Energy, which value has universal validity and applicability.

The table of FIG. 11 shows the results of typical slurry erosion tests conducted on three different metal specimens in accordance with the method and apparatus of the invention. The wear width and depth are shown for three different distances (0.5", 1.0" and 1.5") from the tip of the test specimen 35 designated A, B and C, and the specific energy $E_{sp}$ calculated to remove a unit volume of material at each of these three locations is also shown.

The embodiments of the invention in which an exclusive property or privilege is claimed are defined as follows:

1. A centrifugal slurry erosion testing device including
  a rotatable hollow cylindrical vessel,
  means for feeding a slurry of abrasive particles into the interior of said vessel,
  a specimen holder affixed to and extending radially from said vessel including first and second abutting members the first of which has a cavity in its abutting surface for receiving a specimen of material to be wear tested with a flat surface of the specimen facing the direction of rotation and the second member of which has a shallow, narrow radially extending groove in its abutting surface which communicates with the interior of the rotating vessel and is disposed opposite said flat surface of said specimen and together therewith defines a radial passage for said slurry, and
  means for rotating said cylindrical vessel at high angular velocity about its axis, whereby said slurry is urged by centrifugal force to flow through said passage and said abrasive particles are urged by Coriolis acceleration into a compacted layer against said flat surface and remove material therefrom by scouring action to a measurable depth as the particles flow radially outward, which depth is indicative of the erosion resistance of said specimen.

2. A slurry erosion testing device in accordance with claim 1 wherein said first and second members are of semicylindrical configuration and abut along a planar surface and together define a cylindrical specimen holder.

3. A slurry erosion testing device in accordance with claim 2 wherein said cavity is in the planar abutting surface of said first member and said specimen is affixed in said cavity with the flat surface of said specimen coplanar with said abutting surface and facing the direction of rotation of said vessel.

4. A slurry testing device in accordance with claim 3 wherein said groove is of rectangular cross section in the portion of said second member opposite said cavity so that said radial slurry flow passage formed by said groove together with said flat surface of said specimen is of rectangular cross section.

5. A slurry testing device in accordance with claim 2 wherein said specimen holder includes a tubular sleeve surrounding said abutting semicylindrical first and second members and extending through an aperture in the sidewall of said vessel and having an outwardly extending annular rim interior of said vessel disposed against said vessel sidewall to prevent radially outward movement of said sleeve.

6. A slurry testing device in accordance with claim 5 wherein each of said first and second semicylindrical members has a semiannular outwardly extending shoulder interior of said vessel which is disposed against said annular rim of said sleeve to thereby prevent movement of said specimen holder radially outward from said vessel.

7. A slurry testing device in accordance with claim 6 wherein the radially inward portion of the abutting surfaces of said first and second members have semicylindrical indentations therein extending longitudinally of said abutting members which together define an axial cylindrical channel for flow of said slurry and which communicates at one end with the interior of said vessel and at the other end with said rectangular-in-cross section radial slurry flow passage.

8. A method of erosion testing a material specimen including the steps of
  rotating said specimen with a flat surface thereof facing the direction of rotation,
  concurrently with said rotating step flowing a narrow stream of an abrasive particle slurry in a radial direction across said flat surface, said rotating step being at sufficiently high angular velocity to urge said abrasive particles by Coriolis acceleration into a compacted layer against said flat surface and erode material therefrom by scouring type action as said particles flow radially outward, and said flowing step flowing a predetermined volume of said slurry per unit time and being conducted for a sufficient preselected duration to erode material from said flat surface to a measurable depth which is indicative of the erosion resistance of the specimen material.

9. A method of erosion testing in accordance with claim 8 wherein said flowing step includes confining said slurry stream in a radial passage of rectangular cross section with one longitudinal wall of said passage defined by said flat surface of said specimen.

10. A method of erosion testing in accordance with claim 9 wherein said rotating step includes rotating about its axis a cylindrical vessel having a specimen holder extending radially therefrom provided with a cavity for receiving said specimen and also provided with said radial passage which communicates with the interior of said vessel, and said flowing step includes introducing said abrasive particle slurry into the interior of said vessel.

11. A method of erosion testing a material specimen including the steps of rotating said specimen with a flat surface of said specimen facing the direction of rotation, concurrently with said rotating step wearing material from said flat surface by flowing a narrow stream of an abrasive particle slurry at a predetermined volume per unit time in a radial direction across said flat surface, said rotating step being at sufficiently high angular velocity to urge said abrasive particles by Coriolis acceleration into a compacted mass against said flat surface and erode material therefrom by scouring type action as said particles flow radially outward, continuing said flowing step for a preselected duration of time sufficient to erode material from said flat surface to a measurable depth, and measuring the depth to which said flat surface is worn by said abrasive particles as an indication of the erosion resistance of the material of said specimen.

* * * * *